United States Patent
Flandry, Jr.

(10) Patent No.: US 8,361,074 B2
(45) Date of Patent: Jan. 29, 2013

(54) ADJACENT LEVEL CERVICAL SPINE PLATE

(76) Inventor: Robert E. Flandry, Jr., Spartanburg, SC (US)

( * ) Notice: Subject to any disclaimer, the term of this patent is extended or adjusted under 35 U.S.C. 154(b) by 1273 days.

(21) Appl. No.: 12/150,175

(22) Filed: Apr. 24, 2008

(65) Prior Publication Data

US 2009/0270861 A1    Oct. 29, 2009

(51) Int. Cl.
*A61B 17/58* (2006.01)
*A61B 17/80* (2006.01)

(52) U.S. Cl. .......................... 606/71; 606/286
(58) Field of Classification Search ........... 606/70–71, 606/279–299, 902–906
See application file for complete search history.

(56) References Cited

U.S. PATENT DOCUMENTS

| | | | |
|---|---|---|---|
| 5,603,713 A * | 2/1997 | Aust et al. | 606/279 |
| 6,093,205 A | 7/2000 | McLeod et al. | |
| 6,682,563 B2 | 1/2004 | Scharf | |
| 7,166,111 B2 * | 1/2007 | Kolb et al. | 606/96 |
| 7,186,254 B2 | 3/2007 | Dinh et al. | |
| 7,695,473 B2 * | 4/2010 | Ralph et al. | 606/71 |
| 2005/0107795 A1 | 5/2005 | Morris et al. | |
| 2006/0009845 A1 | 1/2006 | Chin | |
| 2006/0116681 A1 * | 6/2006 | Bert | 606/69 |
| 2006/0122607 A1 * | 6/2006 | Kolb | 606/71 |
| 2006/0235409 A1 | 10/2006 | Blain | |
| 2007/0162021 A1 | 7/2007 | Dinh et al. | |
| 2007/0233108 A1 | 10/2007 | Stalcup et al. | |

* cited by examiner

*Primary Examiner* — Kevin T Truong
*Assistant Examiner* — Larry E Waggle, Jr.
(74) *Attorney, Agent, or Firm* — Cort Flint Monahan & moses LLC

(57) ABSTRACT

A surgical plate system for stabilizing vertebrae of a backbone which includes a first surgical plate, which when connected to adjacent vertebrae of a backbone is constructed to allow attachment with an additional plate which is then interconnectable with a first of the adjacent vertebrae and a third adjacent vertebrae. The connection between the adjacent surgical plates is constructed to allow lateral adjustment between the plates prior to the plates being secured with the vertebrae.

5 Claims, 3 Drawing Sheets

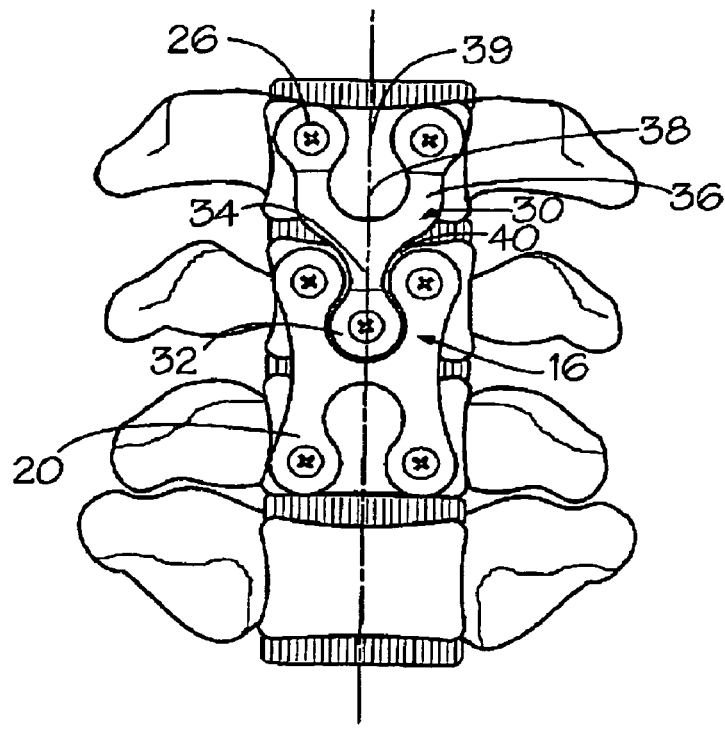
Fig. 4
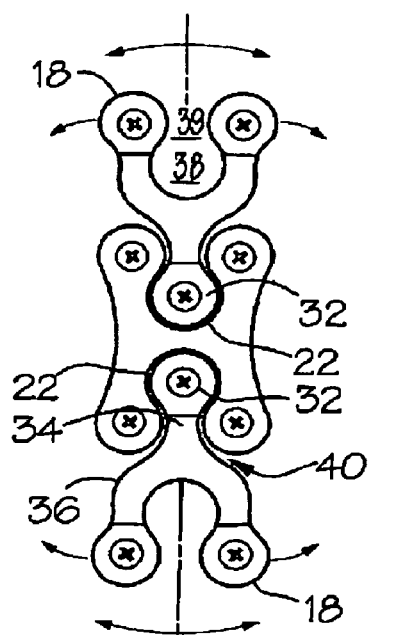 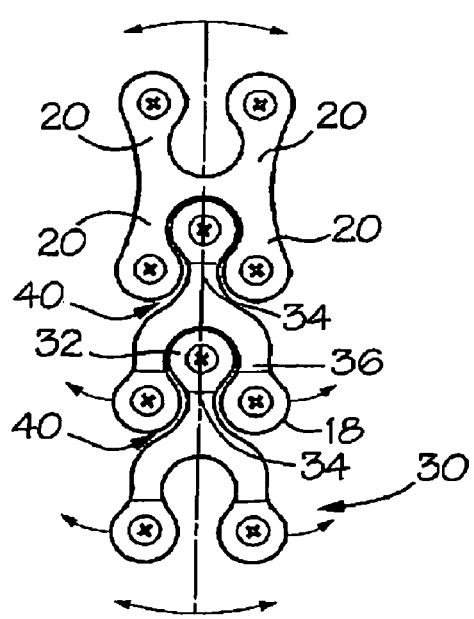
Fig. 5A　　　Fig. 5B

ADJACENT LEVEL CERVICAL SPINE PLATE

BACKGROUND OF THE INVENTION

The instant invention is directed to an anterior cervical tension band or surgical plate system with the capability of plates interconnecting at spaced time periods to stabilize additional vertebrae which have become diseased. This procedure is generally old and known, as is illustrated by the patent to Dinh, et al U.S. Pat. No. 7,186,254 and the publication to Bert, No. 2006/0116681. Neither of these publications recognizes or deals with the problem solved by the instant invention.

In practice, vertebrae separated by a damaged disk must be maintained, separated and be stationarily stabilized. To do this a surgical plate is positioned over a graft and secured by screws with the adjacent vertebrae. Over time, bone and cartilage may grow over, adhere to and cover the surgical plate.

It is common for the disk separating a vertebra adjacent the stabilized vertebra to break down or become diseased, i.e. up to 25% over a five-year period. When this occurs, an additional surgical plate must be installed over the two adjacent of these vertebrae.

Because of growth, as above referred to, it is extremely difficult to remove the installed plate. Further, damage to the vertebrae and surrounding soft tissue is a high probability during such a removal process.

A solution is to install an additional surgical plate adjacent the originally installed surgical plate, as illustrated by the Scharf patent No. 6,682,563. This process raises the risk of vertebra rupture due to the size of the vertebra and the many screws which are longitudinally spaced and inserted into each vertebra.

Another solution is to provide an initial surgical plate to which additional surgical plates can be attached. This arrangement is taught by the referenced patent to Dinh, et al and the publication to Bert.

Again, a problem exists. When installing the initial surgical plate, extreme care must be taken to align the connecting areas of the surgical plates with the longitudinal axis of the backbone. This is extremely difficult due to limited exposure to the entire spine, the particular anatomy or the configuration of each vertebra. It is rare that the first installed surgical plate is aligned true with the vertical axis of the spine.

When the initial plate is slightly misaligned or at a slight angle with the vertical axis, and the condition is not recognized, it can only be exacerbated by the teachings of the referenced publications. These references specifically do not allow lateral adjustment of an additional or joining plate relative to the previously installed plate.

A primary object of the invention is to accomplish segment or vertebrae fixation in a second operation without removal of the existing plate.

Another objective of the invention to provide a system of surgical plates which allow lateral adjustment of the plate being installed and attached to the previously installed plate.

Another object of the invention is a system of surgical plates which may be easily connected with the backbone and which may be easily extended along the spine without removal of initially installed plates.

SUMMARY OF THE INVENTION

The invention is directed to a method of promoting fusion along a backbone in sequential steps between first and second vertebra and then between one of the first and second vertebra and a third vertebra. A first surgical plate interconnects and stabilizes first and second adjacent vertebra. The first plate includes a receiver on at least one end. The receiver comprises a shaped bay of a first circumference which by way of a channel interconnects with an edge of the plate by a channel. The channel is formed at a first width and includes rounded shoulders forming the opening through the edge.

The method further includes providing a generally Y-shaped surgical plate having at one end a shaped head of a second circumference which is less than the circumference of the bay or first circumference. The head is carried by an elongated neck formed of a second width which is less than the first width of the channel. The surgical plate also has at a second end, a bay formed at the first circumference and connected by way of a channel of the first width. The channel is formed by a pair of spaced legs. The method further includes positioning the shaped head and neck of the surgical plate into the channel and bay of the first plate in position over one of the previously connected and fused vertebra while positioning the spaced legs and channel over the third and adjacent vertebra. The legs and channel are laterally adjusted to position the bay of the Y-shaped plate centrally of the vertical axis of the spine or backbone. The Y-shaped surgical plate is then connected to the one of the previously fused vertebra and the third vertebra, fixed in position with the vertebrae.

The method includes providing a second generally V-shaped surgical plate and positioning its head and neck over the third vertebra and into the bay and channel of the above referenced V-shaped surgical plate while positioning its bay and spaced legs over a fourth and adjacent vertebra. Adjusting the bay and legs of the second V-shaped surgical plate laterally to position its bay centrally of the vertical axis of the spine and connecting the surgical plate with the third and fourth vertebra.

The invention includes a system for interconnecting with a pair of adjacent vertebra interconnected with a surgical plate additional adjacent vertebrae. The system comprises the following apparatus and function. A generally H-shaped surgical plate having opposed bay areas each of which are connected through a channel formed by spaced parallel legs. The ends of the channel forming legs are rounded. An opening is provided adjacent end portions of the legs for receiving a screw for securing the H-shaped plate with the adjacent vertebrae.

The channels and the bays are formed of a first size while the heads and necks are formed of a second and smaller size. This structure allows the H-shaped plate to be positioned over adjacent vertebrae, aligned as best possible with the longitudinal axis of the backbone and secured by screws with the associated adjacent vertebrae. The head and neck of the V-shaped connector may then be positioned in a first of the bays and channels of the H-shaped connector with the head positioned over one of the first of the secured vertebra and with the bay and channel forming legs positioned over a third and adjacent vertebra. The V-shaped surgical plate is adjusted laterally to position as best as possible the bay centrally of the longitudinal axis of the backbone and secured with the adjacent vertebra. This aligned along the longitudinal axis of the backbone.

The adjustment along the channel and neck is possible because very slight play is provided between the associated members. Also, the end forming portions of the channel forming legs are rounded or arcuately formed. The Y plate may be adjusted in a lateral direction up to about 15°.

DESCRIPTION OF THE DRAWINGS

FIG. 4 is a sectional top view similar to FIG. 3 showing a Y-shaped surgical plate connected with the first installed H-shaped surgical plate and the adjacent vertebrae FIG. 5A is a top plan view showing the initial H-shaped surgical plate interconnected at opposite ends with a pair of Y-shaped surgical plates.

FIG. 5B is a top plan view similar to FIG. 5A but showing multiple Y-shaped surgical plates extending from a single side of the H-shaped plate.

DESCRIPTION OF A PREFERRED EMBODIMENT

Figure 1:
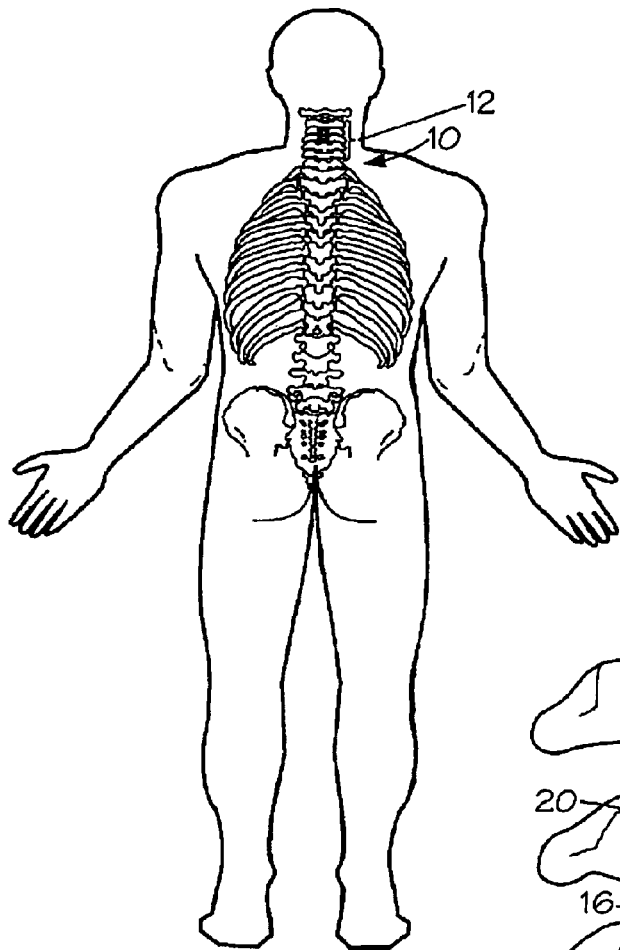
FIG. 1 is a diagrammatic plan view of the backbone.

Turning now to the drawings, FIG. 1 is a diagrammatic view of the vertebrae 10 in which an anterior cervical fusion has been performed by the installation of a surgical plate 12, stabilizing and separating the adjacent vertebrae. Generally, these surgical plates have been formed as a single unit capable of being connected with a pair of adjacent vertebrae 10 as shown in FIG. 2.

Figure 3:
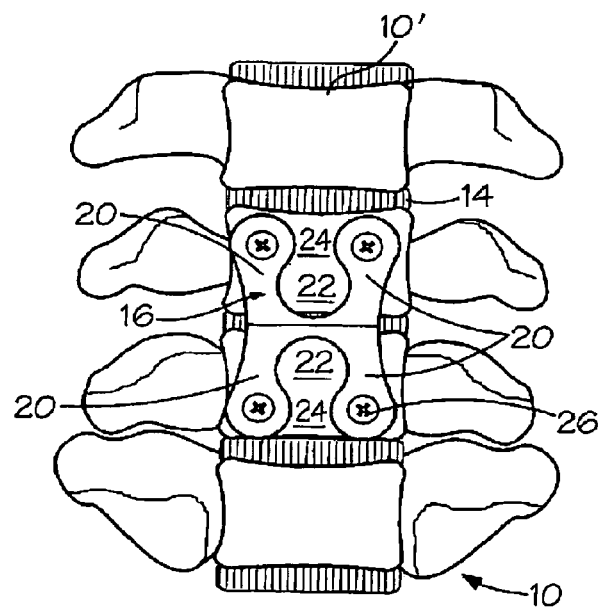
FIG. 3 is a sectional top view similar to FIG. 2 with adjacent vertebrae stabilized with a surgical H-shaped plate of the invention.
Figure 6:
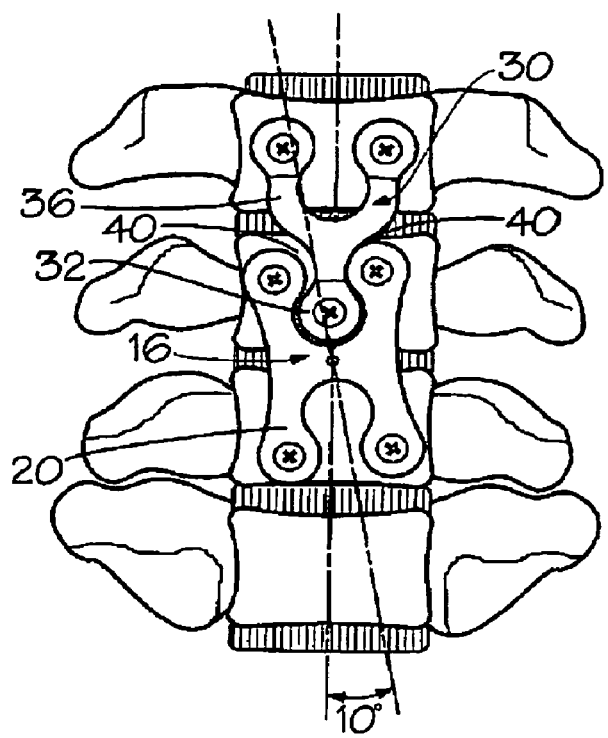
FIG. 6 is a top plan view similar to FIG. 4 showing a misaligned H-shaped plate and the angle of adjustment of the Y-shaped plate.
Figure 7:
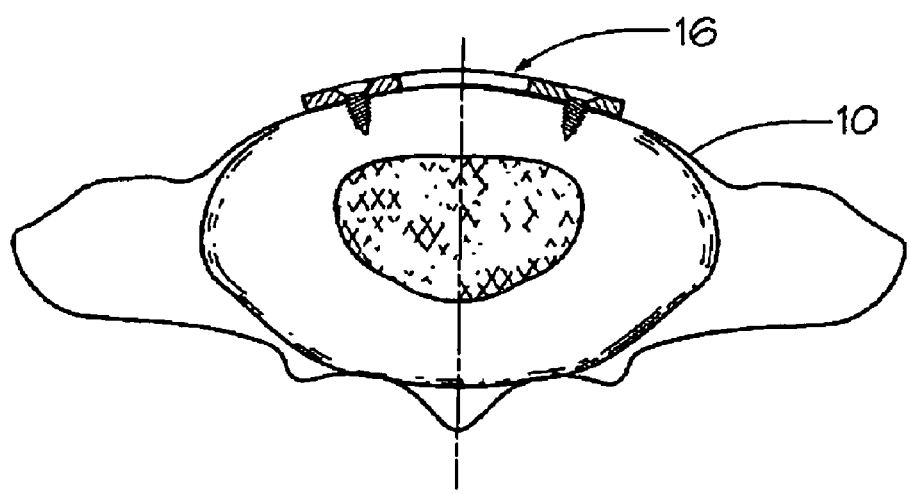
FIG. 7 is a sectional end view of a vertebra and the arcuate shape of the surgical plate.

Turning now to FIGS. 3 and 4, Y-shaped surgical plates 30 and H-shaped surgical plates 12 of the invention are formed of metal to be about 3 cm or greater in length and about 2 cm in width. Each surgical plate is provided with a receiver in the form of bays 22 and 38, which are about 9 mm in diameter. The width of head 32 is about 2 mm less. Channels 24 and 39 are about 5 mm while neck 34 is between about 2 mm and 4 mm. Both H and Y-shaped surgical plates are generally arcuate widthwise as shown in FIG. 7 to generally conform with the surface of the vertebrae. The smaller neck and head fit into the larger bay and channel.

Figure 2:
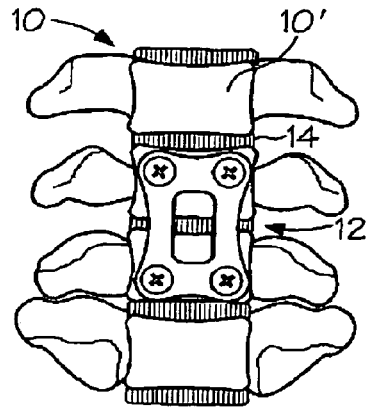
FIG. 2 is a sectional top view of a backbone with adjacent vertebrae stabilized with a known surgical plate.

Records Indicate that about 35% of the disks located on one side with a stabilized vertebra 10, such as disk 14 in FIGS. 2 and 3, have a tendency to deteriorate and rupture after a short period of time because of the additional stress created by the stabilized vertebra. When this occurs, the vertebrae adjacent the stabilized vertebra also must be stabilized.

When a surgical plate, such as 12 in FIG. 2, has been used, that plate must be removed so that a larger plate covering three vertebrae may be inserted. This is a very tedious and sometimes a precarious procedure because bone and cartilage have usually grown over the first attached plate and must be removed during the removal process. Also, removing the screws is extremely difficult, also sometimes resulting in bone damage. Also, it is noted that in most instances one vertebra is not large enough to accommodate end to end surgical plates without a high possibility of bone fracture.

The solution is the surgical plate 16 as shown in FIGS. 3-6. Plate 16 is constructed in a generally H-shape with two pair of oppositely directed generally parallel spaced legs 20 forming bays 22 and a channel 24. Channel 24 terminates between arcuate or rounded end portions of legs 20. Adjacent the arcuate ends of each of legs 20 is provided an opening through which fastening screws 26 are passed and attached in the associated vertebrae 10. It is noted that the center of each bay 22 along with position of screws 26 is located away from the edge of the associated vertebrae so as to prevent bone rupture.

Should the disk supporting an adjacent vertebra, such as 10' in FIG. 3, become diseased or deteriorated to an extent that this vertebra needs to be stabilized, the procedure is much simplified using the instant system.

A mating Y-shaped surgical plate 30 is provided. This Y-shaped plate comprises at one end a head 32 carried by neck 34. A pair of spaced arms 36, which merge and connect with the end of neck 34. Arms 36 form adjacent their upper ends bay 38 and along their length and channel 39. The outer ends 18 of arms 36 are rounded.

In order to install the V-shaped surgical plate 30, only growth which may cover bay 22 and channel 24 of the previously installed H-shaped surgical plate and neck 34 of V-shaped surgical plate 30 are positioned in bay 22 and channel 24 of H-shaped plate and in position over the associated vertebra while legs 36 forming bay 38 of V-shaped surgical plate 16 are positioned over the adjacent vertebrae. Screws 26 are passed through appropriate holes to secure V-shaped surgical plate 30 with the associated vertebrae.

Critical to this invention is the space or gap 40 formed between the inner walls of the lower ends of legs 20 and 36. These lower ends are rounded or formed arcuate so as to engage evenly with the outer walls of neck 34. It is preferred that a space of at least 2 mm form gap 40 and separate inner walls of the forming legs channels 24 and 39 so that Y-shaped plate 30 may be moved laterally relative to the fixed surgical plate to which it is connected as indicated by the arrows in FIGS. 5A, 5B and 6 up to about 15°.

It is the intent that H-shaped surgical plate 16 when initially installed be positioned along the backbone so that legs 20 extend generally parallel with the vertical axis of the backbone. It has been found that either due to difficulty or circumstances during installation of the plate or due to shifting over time, that this ideal position is not always obtainable. Therefore, for an extended plate such as Y-shaped plate 30, to not be further offline, it is necessary that the Y-shaped plate be capable of lateral adjustment relative to the axis of the stationary H-shaped plate and the backbone. This allows for an indeterminate number of additional plates to be attached and be maintained substantially aligned with the backbone.

While a preferred embodiment of the invention has been described using specific terms, such description is for illustrative purposes only, and it is to be understood that changes and variations may be made without departing from the spirit or scope of the following claims.

What is claimed is:

1. A surgical plate system adapted to be sequentially secured with vertebrae of a backbone for stabilizing said vertebrae comprising:
 (a) a generally H-shaped surgical plate including:
  a pair of legs extending on opposing sides of said surgical plate between upper and lower ends of said plate;
  said pair of legs being spaced apart at said upper and lower ends of said surgical plate, and contoured open bays formed between said spaced apart legs;
  channels opening into said bays at said upper and lower ends of said surgical plate, said channels being reduced in width relative to said bays;
 (b) a generally Y-shaped surgical connector plate including:
  a pair of spaced legs converging into a tingle leg;
  said pair of legs being spaced apart at first end of said connector plate, and a contoured open bay formed between said spaced apart legs at said first end;
  said single leg having a neck adjoining said spaced legs and terminating an outer head at a second end of said Y-shaped connector plate, and said head shaped to fit within one of said surgical plate bays and said connector plate bay; and a channel formed between said spaced legs at said first end of said Y-shaped connector plate, said channel being reduced in width relative to said bay;

(c) said surgical plate being adapted to be positioned over and secured with first and second adjacent ones of said vertebrae;

(d) said Y-shaped connector plate being adapted to have said head and neck positioned in a selected one of said surgical plate bays and channels, and being attached to a selected one of said first and second vertebrae with said connector plate legs positioned over a third adjacent vertebra;

(e) said bays and channels of said surgical plate being of a width sufficient to define a gap which allows lateral movement between said neck and head of said connector plate and said surgical plate channels and bays for angular adjustment; whereby said plate may be angularly adjustable by lateral movement so that said connector plate can be aligned with the longitudinal axis of said backbone prior to being secured with said third and selected vertebrae.

2. The system of claim 1 wherein said channel is sized to be about 2 mm larger than the width of said neck.

3. The system of claim 1 wherein said bays of said surgical plate and said connector plate are about 2 mm greater than the head of said connector plate.

4. The system of claim 1 wherein lateral movement of said Y-shaped connector plate relative to said H-shaped plate may be adjusted up to 15°.

5. The system of claim 1 wherein end portions of said legs are arcuate in cross-section.

* * * * *